United States Patent [19]

Obermeier et al.

[11] Patent Number: 4,677,192
[45] Date of Patent: Jun. 30, 1987

[54] PROCESS FOR THE SEPARATION OF MIXTURES OF INSULIN, INSULIN DERIVATIVES AND, WHERE APPROPRIATE, IMPURITIES

[75] Inventors: Rainer Obermeier, Hattersheim am Main; Volker Teetz, Hofheim am Taunus; Jürgen Ludwig, Brachttal, all of Fed. Rep. of Germany

[73] Assignee: Hoechst Aktiengesellschaft, Frankfurt am Main, Fed. Rep. of Germany

[21] Appl. No.: 804,325

[22] Filed: Dec. 4, 1985

Related U.S. Application Data

[63] Continuation of Ser. No. 552,753, Nov. 17, 1983, abandoned, which is a continuation-in-part of Ser. No. 445,849, Dec. 1, 1982, abandoned.

[30] Foreign Application Priority Data

Dec. 3, 1981 [DE] Fed. Rep. of Germany ....... 3147842

[51] Int. Cl.$^4$ .................... A61K 37/26; C07K 7/40
[52] U.S. Cl. .................................................. 530/305
[58] Field of Search ..................... 260/112.7; 530/305

[56] References Cited

FOREIGN PATENT DOCUMENTS 0002492  1/1978  Japan ............................. 260/112.7

OTHER PUBLICATIONS

*Arh. Hig. Rada*–Meniga et al., 14(1963), 165–169.
Pickart et al.–*Prep. Biochem.* 5, 397–412, 1975.
Chrambach et al., *J. Biol. Chem.*, 235, 3478–3483, (1960).
Carpenter et al.,–*Biochem.* 2, 1272–1277, (1963).
"Bioresearch and Chromatography Products", Pierce Eurochemie, B.V. Rotterdam, p. 194.
"The Chemist's Companion", Wiley-Interscience, New York (1975), p. 370.
"Reagenzien Diagnostica Chemikalien", 1980, E. Merck, Darmstadt, pp. 328 & 358.
Porath et al., Biochim. Biophys. Acta 13, 268–277 (1954).
Organikum, VEB Deutscher Verlag der Wissenschaften, Berlin, 1973, 12th Ed., p. 79.

*Primary Examiner*—Frederick E. Waddell
*Attorney, Agent, or Firm*—Curtis, Morris & Safford

[57] ABSTRACT

A method for separating insulin or certain insulin derivatives from mixtures containing the same by chromatography of the mixture on a column filled with silica gel having a particle size between 40 and 500 microns with an eluant mixture comprising chloroform, methanol, water and triethylamine.

11 Claims, No Drawings

PROCESS FOR THE SEPARATION OF MIXTURES OF INSULIN, INSULIN DERIVATIVES AND, WHERE APPROPRIATE, IMPURITIES

This is a continuation application of Ser. No. 552,753 filed Nov. 17, 1983, now abandoned, which in turn is a continuation-in-part application of U.S. patent application Ser. No. 445,849, filed Dec. 1, 1982, and now abandoned.

The conversion in a semi-synthetic manner of natural pig insulin into human insulin by chemical or enzymic exchange of the alanine in position B 30 for threonine has been disclosed. Obermeier, R., Geiger, R. Hoppe-Seyler's Z. physiol. Chemie 357, 759–767 (1976), Ruttenberg, M. A. Science 177 623–626 (1972), Morihara, K., Oka, T., Tsuzuki, H. Nature 280, 412–413 (1979), Inouye, K. J. Am. Chem. Soc. 101, 751–752 (1979), Schmitt, E., Gattner, H. G. Hoppe-Seyler's Z. physiol. Chem. 359, 799–802 (1978) and Bromer, W. W., Chance, R. E. Biochem. Biophys. Acta 133, 219–223 (1967). The aim of this conversion is to be able for immunological reasons to use insulin from the same species in the treatment of human diabetes mellitus.

The advantages of this treatment can only be achieved when it is possible reliably to separate insulin derivatives and impurities from human insulin in the crude material from the semi-synthetic process.

The known methods of separation are not suitable for reliably ensuring the separation of human insulin from pig insulin components. It can be deduced from the aminoacid anylses published in the literature that contamination with pig insulin up to an order of magnitude of 25% is possible in semi-synthetic human insulin.

In order to prevent even trace contamination of human insulin with pig insulin or enzymes by the repeated use of packing materials for chromatography columns, which can be regenerated, a cheap disposable material having an optimal separation efficiency is desirable as a column packing. In analytical high pressure liquid chromatography (HPLC), high-resolution chromatographic separations are achieved on hydrophobic silica gel which has been derivatized with organic moieties (reversed phase). Pickart, Thaler, Preparative Biochemistry 5 [1975] 397–412 propose a method for the purification of somatomedin-C insulin-like activity and $^{125}$I-bovine insulin by high pressure liquid chromatography (HPLC) on columns prepacked with silica gel of 10 micron size using an eluant mixture consisting of methanol, water and formic acid. It is taught at the top of page 403 that silica gel of 30–44 micron size was not useful in separating peptides or proteins. However, the high costs of these HPLC sorbents prohibit their use as disposable column packaging materials.

It has now been found that the chromatographic separation of crude mixtures from enzymic semi-synthetic processes for insulin on columns which are packed with commercially available silica gel, using certain mixtures of organic solvents, such as, for example, chloroform or methylene chloride:methanol:water:triethylamine:formic acid, is superior to all other methods of separation. This superiority results, on the one hand, from the differences in the retention times, some of which are large, of the components of the mixtures to be separated, and on the other hand from the rapidity of running a column. The costs of the silica gel, which is discarded after one run, can be ignored compared to those of the processed insulin.

Thus the invention relates to a process for the separation of mixtures of insulin, insulin derivatives and possible impurities by chromatography of the mixture in a column filled with a silica gel having a particle size between 40 and 500 microns, preferably between 40 and 125 microns, using an eluant mixture comprising chloroform, methanol, water and triethylamine.

"Insulin" is understood to mean human insulin or animal, in particular mammalian, insulin (e.g., porcine insulin).

"Insulin derivative" is understood to mean degradations products of insulin, insulin esters and or other protected insulins (e.g. human insulin-B30-(But)$_2$ or B$_1$-BOC-human insulin-30-(But)$_2$).

The process is particularly suitable for the purification of insulin and for the separation of insulin or its degradation products from trypsin or similar enzymes and insulin esters or other insulin derivatives.

All commercially available silica gels for column chromatography having a particle size between 40 and 500 microns are suitable as a column packing, for example the commercial product "Kieselgel 60" from Merck & Co., Darmstadt, available in particle sizes between 40 and 500 microns.

For the chromatography, it is possible to use as the eluant all those mixtures of eluants in which insulin esters or derivatives on the one hand and insulin or its degradation products on the other hand exhibit differing Rf values on commercially available thin layer chromatography plates. Particularly good separation effects are achieved when the crude product is chromatographed in an eluant mixture composed of 1,500–2,100 parts by volume of chloroform, 1,000–1,500 parts by volume of methanol, 350–450 parts by volume of water, 35–55 parts by volume of triethylamine and 0–15 parts by volume of formic acid. The eluant mixture may furthermore contain 0–1800 parts by volume of methylene chloride and/or 0–350 parts by volume of a 2-[(C$_1$–C$_4$)-alkoxy]-ethanol, preferably 2-methoxyethanol(methylglycol).

The process is particularly advantageous for the separation of human insulin-B 30 -di-tert.-butylthreonine from pig insulin and trypsin, a mixture which arises in the enzymic conversion of pig insulin into human insulin.

USE EXAMPLES 1.4 g of a mixture of 70% human insulin-B 30-di-tert.butylthreonine and 30% pig insulin are dissolved in 20 ml of a solvent composed of chloroform:methanol:water:triethylamine:formic acid=1,800:1,500:375:45:9 (v/v) and applied using a disposable syringe onto a dry size C Lobar ® ready-packed column (particle size of silica gel is between 63 and 125 microns). The column is developed with the same solvent. After the solvent front has appeared, individual fractions (10 ml) are collected.

Human insulin-B 30-(But)$_2$ appears in fractions 37–53. These are combined and concentrated to a volume of 30–50 ml on a rotary evaporator. About 500 ml of acetone are added to this solution and the precipitated product is isolated by centrifugation.

The pig insulin is eluted in the fractions 120–137 and is isolated as described above. The two products are dried under slight vacuum.

Yield: 2.59 g of human insulin-B 30-(But)$_2$; 1.03 g of insulin (P)

2. N-αB1-tert.-Butyloxycarbonyl-B30-di-tert.-butyl-threonine-insulin (4 g) are dissolved as in Example 1 and applied to a column (2.5×50 cm) filled with 300 g of silica gel "Kieselgel 60" having a particle size between 40 and 63 microns, which has been equilibrated with chloroform. The column is eluted with the same solvent mixture as in Example 1. The peak appearing first contains B1-BOC-insulin-B30-(But)2, and pig insulin is eluted in the late fractions. The working up is as in Example 1.

3. A mixture as in Example 1 (4 g) is applied to a Lobar ® ready-packed column C equilibrated with 70% ethanol/30% tris buffer (0.05M, pH 8.0), and is chromatographed with the same eluant. The appropriate fractions, which contain human insulin B30-di-tert.-butylthreonine and pig insulin separated from one another, are worked up as in Example 1.

4. Impure pig insulin (4 g) is dissolved in a mixture of chloroform:methanol:water:triethylamine:formic acid = 1,200:1,100:370:47:11 and chromatographed on a silica gel column as in Example 2. The eluate, which is fractionated in 10 ml portions, is worked up as in Example 1. Fractions which, after checking by HPLC and polyacrylamide gel electrophoresis, contain pure pig insulin are combined.

Yield: 3.61 g.

5. A mixture as in Example 1 (4 g) is applied to a column (2.5×50 cm) packed with 500 g Grace ® silica gel 50 (average particle size 50 microns) in methylene chloride. The eluant is composed of chloroform:methylene chloride:methanol:water:triethylamine:formic acid = 900:900:1500:375:45:9 (vol./vol.). Fractions are collected and isolation of the products is performed as described in Example 1.

Yields: 2.65 g human insulin-B30-(Bu$^t$)2; 1.1 g porcine insulin 6. 3.8 g of a reaction mixture obtained by splitting off the protective groups of semisynthetic human insulin-B30-(Bu$^t$)2 by means of trifluoro-acetic acid is applied to a column (2.5×50 cm), filled with 300 g "Kieselgel 60" having a particle size between 63 and 200 microns, which has been equilibrated with chloroform. The column is eluted with a mixture composed of chloroform:methanol:water:triethylamine:formic acid:2-methoxyethanol = 1,500:1,400:450:55:14:190 (vol./vol.). The appropriate fraction, which contains human insulin, is worked up as in Example 1. Yield: 2.5 g human insulin.

We claim:

1. A method for the recovery of a human insulin ester and pig insulin from a mixture containing then and resulting from an enzymic conversion of pig insulin into human insulin ester, which method comprises chromatographing said mixture on a column filled with silica gel having an average particle size between 40 and 125 microns using an eluant mixture comprising, in parts by volume, 1500–2100 parts of chloroform, 1000–1500 parts of methanol, 350–450 parts of water, 35–55 parts of triethylamine, and more than 0 and up to 15 parts of formic acid, and recovering the pig insulin and the human insulin ester from the eluate in different fractions, the enzyme remaining absorbed on the silica gel column.

2. A method for the recovery of a human insulin ester and pig insulin from a mixture containing them and resulting from an enzymic conversion of pig insulin into human insulin ester, which method comprises chromatographing said mixture on a column filled with silica gel having an average particle size between 40 and 125 microns using an eluant mixture comprising, in parts by volume, 1500–2100 parts of chloroform, 1000–1500 parts of methanol, 350–450 parts of water, 35–55 parts of triethylamine, more than 0 and up to 15 parts of formic acid, and more than 0 and up to 350 parts of a 2-($C_1$–$C_4$-alkoxy)-ethanol, and recovering the pig insulin and the human insulin ester from the eluate in different fractions, the enzyme remaining absorbed on the silica gel column.

3. A method for the recovery of human insulin from a mixture resulting from an enzymic conversion of pig insulin into human insulin and containing pig insulin and a human insulin ester, which method comprises chromatographing said mixture on a column filled with silica gel having an average particle size between 40 and 125 microns using an eluant mixture comprising, in parts by volume, 1500–2100 parts of chloroform, 1000–1500 parts of methanol, 350–450 parts of water, 35–55 parts of triethylamine, and more than 0 and up to 15 parts of formic acid, whereby said pig insulin and human insulin ester are eluted in different fractions, subjecting said human insulin ester fraction to acid cleavage with trifluoroacetic acid, and then chromatographing the cleavage product again on a column filled with silica gel having an average particle size between 40 and 125 microns using an eluant mixture comprising, in parts by volume, 1500–2100 parts of chloroform, 1000–1500 parts of methanol, 350–450 parts of water, more than 0 and up to 15 parts of formic acid, more than 0 and up to 350 parts of a 2-($C_1$–$C_4$-alkoxy)-ethanol, and 35–55 parts of triethylamine, whereby human insulin and unreacted ester in said cleavage product are eluted in different fractions.

4. A method for separating human insulin from a human insulin ester, which method comprises chromatographing a mixture containing said insulin and said ester on a column filled with silica gel having a particle size between 40 and 500 microns using an eluant comprisng, in parts by volume, 1500–2100 parts of chloroform, 1000–1500 parts of methanol, 350–450 parts of water, more than 0 and up to 15 parts of formic acid, and 35–55 parts of triethylamine, whereby said insulin and said ester are eluted in different fractions.

5. A method as in claim 1 wherein said silica gel has a particle size between 40 and 63 microns.

6. A method as in claim 1 wherein said silica gel has a particle size between 63 and 125 microns.

7. A method as in claim 1 wherein said ester is human insulin B30-(Bu$^t$)2.

8. A method as in claim 1 wherein human insulin B30-(Bu$^t$)2 is separated from a mixture containing the same together with pig insulin and trypsin.

9. A method for the recovery of a human insulin ester and pig insulin from a mixture containing them and resulting from an enzymic conversion of pig insulin into human insulin ester, which method comprises chromatographing said mixture on a column filled with silica gel having a particle size between 40 and 500 microns using an eluant mixture comprising, in parts by volume, 1500–2100 parts of chloroform, 1000–1500 parts of methanol, 350–450 parts of water, 35–55 parts of triethylamine and more than 0 and up to 15 parts of formic acid, and at least one component selected from the group consisting of 0–1800 parts of methylene chloride, and 0–350 parts of a 2-($C_1$–$C_4$-alkoxy)ethanol.

10. A method as in claim 4 wherein said eluant mixture additionally comprises a 2-($C_1$–$C_4$-alkoxy)ethanol.

11. A method as in claim 4 wherein said eluant mixture additionally comprises 2-methoxyethanol.

* * * * *